Figure 1:
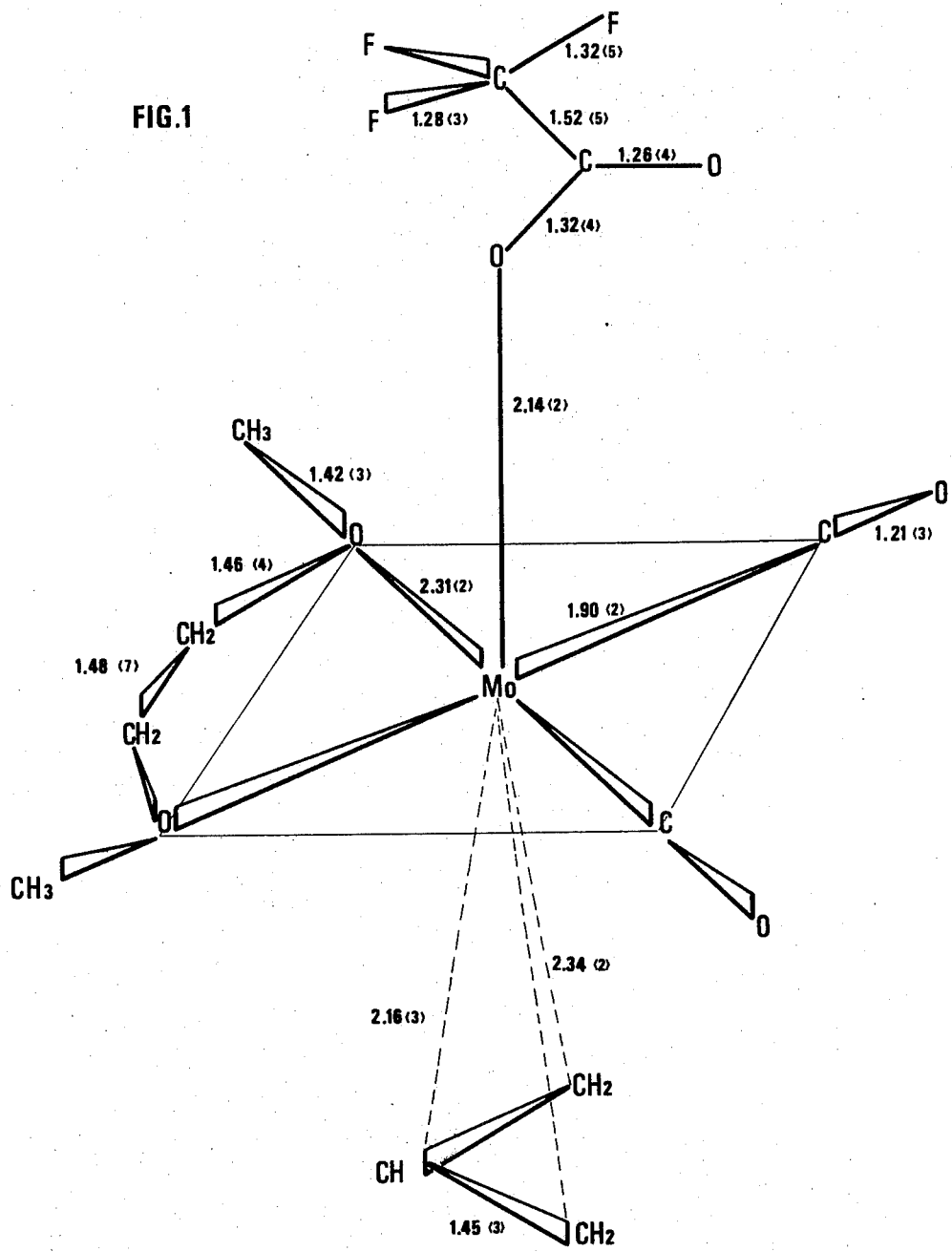

United States Patent [19]
Dawans et al.

[11] 3,931,242
[45] Jan. 6, 1976

[54] NEW MOLYBDENUM AND TUNGSTEN COMPOUNDS, THEIR MANUFACTURE AND THEIR USE AS CATALYSTS IN THE STEREOSPECIFIC POLYMERISATION OF UNSATURATED ORGANIC COMPOUNDS

[75] Inventors: Francois Dawans, Bougival; Emmanuel Goldenberg, Poissy, both of France

[73] Assignee: Institut Francaise du Petrole, des Carburants et Lubrifiants, Paris, France

[22] Filed: Dec. 28, 1973

[21] Appl. No.: 429,209

Related U.S. Application Data

[63] Continuation-in-part of Ser. No. 215,425, Jan. 4, 1972, abandoned.

[30] Foreign Application Priority Data

Jan. 8, 1971 France .............................. 71.00583
Jan. 8, 1971 France .............................. 71.00584

[52] U.S. Cl.... 260/346.1 M; 260/340.6; 260/340.7; 260/429 R; 260/429 L; 260/429 J; 260/89.5 A; 260/92.8 R; 260/93.5 R; 260/94.3; 260/93.1; 252/431 C

[51] Int. Cl.² ......................................... C07F 11/00
[58] Field of Search ................................. 260/347.3

[56] References Cited
UNITED STATES PATENTS
3,660,445   5/1972   Dawans .......................... 260/439 R

*Primary Examiner*—Harry I. Moatz
*Attorney, Agent, or Firm*—Millen, Raptes & White

[57] ABSTRACT

Organic compounds of the formula:
$$[(H_{3-n}X_n)C - CO_2M(CO)_m(R)_p(L)_q]_r$$
in which X is a halogen atom, at least one X being fluorine, M is molybdenum or tungsten, R is a hydride ion or a hydrocarbon group, L is a Lewis base and $m$, $n$, $p$, $q$ and $r$ are integers, are manufactured from fluoracetic esters and molybdenum or tungsten carbonyl compounds. They are useful as catalysts for polymerizing or co-polymerising unsaturated compounds such as butadiene.

7 Claims, 2 Drawing Figures

NEW MOLYBDENUM AND TUNGSTEN COMPOUNDS, THEIR MANUFACTURE AND THEIR USE AS CATALYSTS IN THE STEREOSPECIFIC POLYMERISATION OF UNSATURATED ORGANIC COMPOUNDS

CROSS REFERENCE TO RELATED APPLICATION

This application is a continuation-in-part of copending application Ser. No. 215,425, filed Jan. 4, 1972 now abandoned.

This invention relates to the manufacture and use of a new catalytic composition which may be used in the stereospecific polymerisation and copolymerisation of unsaturated compounds, particularly conjugated dienes.

These catalysts have the following formula:

$$[(H_{3-n}X_n)C-CO_2M(CO)_m(R)_p(L)_q]_r$$

in which X is a halogen atom, at least one of the Xs being fluorine; $n$ is an integer which is selected from 1, 2 and 3; M is molybdenum or tungsten; R is an hydride ion or a hydrocarbon radical, for example an alkyl radical, an allylic radical, or an aralkyl or aryl radical; L is a Lewis base which contains at least one ether, alcohol or ketone group; $m$ is an integer from 1 to 4; $p$ and $q$ are integers selected from 1 and 2; and $r$ is an integer, preferably 1 or 2.

In the foregoing formula, numerals $m$, $p$, and $q$ are related to one another according to the 18 electron-rule, as set forth, for example, by G. E. Coates et al in "Principles of organometallic Chemistry" (Methuen and Co, London 1968) pp 150–153 and by G. E. Coates et al in "Organometallic Compounds" (Methuen and Co, London 1956) Vol 2, page 2. Indeed, the compounds of this invention, which contains such ligands as carbonyl groups, hydrocarbon radicals or hydride ion, and certain other organic ligands, and are isolable at room temperature, can be regarded as having 18 electrons in the valence shell of the metal, thus complying with the rule; "a valence shell containing 18 electrons gives rise to stable compounds". Moreover, in the present case, the unsophisticated 18 electron-rule is also confirmed by X-ray diffraction patterns, performed on the crystalline compounds, and providing a detailed insight into the chemistry of the new organometallic complexes of this invention.

The application of the 18 electron-rule to the compounds of this invention can be done by counting the electrons in the valence shell of the metal as follows: The number of electrons contributed by molbdenum or tungsten is 6. The number of electrons which the ligands formally contribute to the metal, according to the conventional classification of ligands is: 1 for alkyl radicals, hydride ions or acetate groups; 2 for carbonyl, ether groups, alcholic hydroxy, or ketone groups; and 3 for $\pi$-allylic groups. By adding the number of electrons contributed by the ligands to the number of electrons contributed by the metal, the sum found is 18. This procedure may be exemplified by the following compounds:

| Structure of the complex | | | | Number of electrons |
|---|---|---|---|---|
| Acetate | W (CO)$_2$ | ($\pi$—C$_3$H$_5$) | (diether) | |
| 1 | 6 2×2=4 | 3 | 2×2=4 | = 18 |
| Acetate | Mo (CO)$_3$ | ($\pi$—C$_3$H$_5$) | (monoether) | |
| 1 | 6 3×2=6 | 3 | 2 | = 18 |
| Acetate | Mo (CO)$_3$ | ($\pi$CH$_3$) | (diether) | |
| 1 | 6 3×2=6 | 1 | 2×2=4 | = 18 |

-continued

| Structure of the complex | | | | Number of electrons |
|---|---|---|---|---|
| Acetate | Mo (CO)$_3$ | ($\pi$—C$_3$H$_5$) | (monoketone) | |
| 1 | 6 3×2=6 | 3 | 2 | = 18 |
| Acetate | Mo (CO)$_3$ | (H) | (monoether)$_2$ | |
| 1 | 6 3×2=6 | 1 | 2×2=4 | = 18 |

Most of these compounds are solid, frequently crystalline products, which may be easily obtained in the pure state by a process according to this invention, in one step, using reactions which do not require handling of flammable organometal compounds. They have a fairly good stability under inert atmosphere, which makes their storage easier, and they are sufficiently soluble in various media to be easily handled and used in the form of solutions.

The new molybdenum and tungsten compounds of this invention may be obtained with high yields, for example by reacting carbonyl derivatives of the corresponding metals with esters of fluoracetic acids in the presence of at least one stoichiometrical amount of a Lewis base containing at least one ether, alcohol or ketone group.

The easily available molybdenum and tungsten hexacarbonyl compounds of the formulae Mo(CO)$_6$ and W(CO)$_6$ are preferably used.

The following esters of fluoracetic acids are examples of reactants which may be used for manufacturing compounds according to this invention: the methyl, ethyl, allyl, methallyl, crotyl, phenyl and benzyl esters of mono-, di- or tri-fluoracetic acid, of mono-fluoro-dichloracetic acid, mono-fluoro-dibromacetic acid, difluoro-monochloracetic acid and difluoro-monobromacetic acid. According to a particular embodiment, the allyl ester of trifluoracetic acid may be used to obtain new compounds according to this invention with very high conversion rates.

The Lewis base with at least one ether, alcohol or ketone group is preferably tetrahydrofuran, 1,2-dimethoxy ethane, ethylene glycol monomethyl ether, dioxane, di-isobutyl ether, diethylene glycol diethyl ether, acetone, methylethylketone and acetylacetone.

The esters of the fluoracetic acids and the Lewis base may be used in stoechiometrical amount with respect to the molybdenum or tungsten compound or in any other proportion, according to the nature and the desired conversion rate of the reactants. They are preferably used in at least a stoichiometric amount, with respect to the molybdenum or tungsten compound.

Various reaction media may be used, for example ethers, esters, ketones, aliphatic hydrocarbons, aromatic hydrocarbons or halogenated hydrocarbons. Ethers are preferably used since they result in higher reaction rates.

The manufacture of the new compounds of this invention may be improved either by heating the reaction mixture at a temperature in the preferred range of from 50° to 150°C or in a somewhat different range, or by a photochemical treatment, for example by irradiating the reaction mixture with U.V. rays.

The preferred reaction times are usually in the range of from 15 minutes to 48 hours; they depend on the particular activation treatment employed, the nature and the concentration of the reactants and the desired conversion rate.

The new compounds of this invention may be used as catalysts in the polymerisation of straight-chain or cyclic ethylenic unsaturated organic monomers, containing, for example, from 2 to 8 carbon atoms. They are particularly useful in the stereospecific polymerisation of linear conjugated dienes such as 1,3-butadiene, isoprene and piperylene, vinylic monomers such as styrene, vinyl chloride and methyl methacrylate, and also in the polymerisation of cyclic ethylenic unsaturated monomers such as cyclopentene and 1,5-cyclooctadiene to obtain straight-chain polymers.

According to a particular embodiment, the invention relates to a process for producing polybutadiene with a high content both of cis-1,4 and 1,2 units and substantially no trans-1,4 unit. In a preferred embodiment, the polymers of 1,3-butadiene obtained according to this invention contain from 55 to 85% of 1,2-vinyl units, from 45 to 15% of cis-1,4 units and less than 3% of trans-1,4 units. They have glass transition temperatures usually between $-25°$ and $-80°C$.

The invention may be also applied to the copolymerisation of two or more unsaturated ethylenic monomers.

The polymerisation process of this invention may be carried out at temperatures for example between $-20°$ and $+100°C$. Temperatures between $25°$ and $75°C$ are preferred, although higher and lower temperatures are also convenient.

The polymerisation is preferably carried out in the presence of a paraffinic or aromatic hydrocarbon such as normal heptane, iso-octane, cyclohexane, benzene or toluene.

The polymerisation reaction may be carried out under autogeneous pressure or under any other pressure, provided it is high enough to maintain the reaction mixture substantially in liquid phase. The pressure depends of the monomer, the particular diluent and the temperature at which the polymerisation is carried out.

The polymerisation process may be carried out batchwise or continuously by maintaining the necessary concentrations of catalyst in the reactor for an appropriate time which depends on the temperature, the pressure and the concentration of catalyst and monomer(s).

When the radical R is allyl, another embodiment consists of using, instead of the isolated catalyst of the above general formula, a mixture of the reactants which may be employed for manufacturing it. This mixture may be introduced into the vessel which contains the monomer(s) and the polymerisation diluent if any.

In that case, the molar ratio of the molybdenum or tungsten compound to the allyl ester of the haloacetic acid may be in the range of from 0.25 : 1 to 10 : 1, preferably from 0.9 : 1 to 2 : 1, these limits being not imperative, and the concentration of the molybdenum and tungsten compounds may vary broadly; it is advantageously in the range of from $0.5 . 10^{-3}$ to $5 . 10^{-2}$ mole per liter of reaction mixture.

The polymers and copolymers of this invention may be liquid or solid according to their nature and their polymerisation degree; they have usually interesting properties in view of their use as plasticized materials or modified elastomers, either alone or as mixtures.

For example, the polybutadienes obtained according to this invention may be used with advantage as additives in pliable coatings or paints, or as mixtures in rubbers (they modify the ageing properties and rebound elasticity thereof) or in plastic materials (they improve the operability and impact resistance thereof).

Finally, the liquid or semi-solid polybutdienes which may be obtained according to this invention and which have a number average molecular weight of a most 50,000 may be used for the manufacture of thermosettin resins, which may be processed like thermoplastic materials, since their curing rate is high.

The invention is illustrated by the following examples which are in no manner intended to limit the scope thereof.

EXAMPLE 1

10 grams of molybdenum hexacarbonyl of the formula $Mo(CO)_6$ are added to a solution of 5.1 ccm of allyl trifluoracetate of the formula $CF_3COOC_3H_5$ in 378 ccm of 1,2-dimethoxy ethane. The concentration of the molybdenum compound is thus 0.1 mole per liter of reaction mixture and the ester is used in equimolecular proportion with respect to molybdenum. The mixture is stirred at $80 \pm 2°C$ under inert atmosphere for 8 hours; it progressively turns brown-orange. The reaction mixture is then cooled down to $-50°C$, decanted, concentrated by half by evaporation of the solvent under reduced pressure and finally crystallized at about $-20°C$ for 12 hours. The orange crystals separate by filtration; they are washed several times at low temperature with ethyl ether and optionally recrystallized in 1,2-dimethoxy ethane.

There is finally obtained 7.4 grams of a crystalline product of yellowish-orange colour whose elemental analysis is in agreement with the formula $MoC_{11}H_{15}O_6F_3$. This compound has been subjected to infra-red and nuclear magnetic resonance analysis and found to have the following structure:

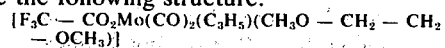

which is confirmed by the X-ray diffraction pattern of this compound.

2.34 grams of this compound are added to a solution of 270 grams of 1,3-butadiene in 1480 ccm of toluene. The conversion is practically complete in 30 minutes at $40°C$ and there is recovered a liquid polybutadiene whose vitrous transition temperature is $-56°C$, as determined by differential thermal analysis; the polymer has been analysed by infra-red spectrometry and magnetic nuclear resonance and found to contain 76% of 1,2-units and 24% of cis-1,4 units; the intrinsic viscosity, as determined at $30°C$ in toluene, is 0.94 dl/g.

EXAMPLE 2

A mixture of 0.63 g of molybdenum hexacarbonyl, 0.32 ccm of allyl trifluoracetate and 23 ccm of 1,2-dimethoxy ethane is stirred at $80° \pm 2°C$ for 4 hours. It is then dried off under reduced pressure and a solution of 27 g of 1,3-butadiene in 148 ccm of toluene is added thereto. After 30 minutes stirring at $40°C$, the conversion rate is 84% and there is obtained a polymer whose intrinsic viscosity, as determined at $30°C$ in toluene, is 0.64 dl/g. The microstructure of the resulting polybudadiene consists of 78% of 1,2 vinyl units and 22% of cis-1,4 units; no trans-1,4 unit can be detected. The glass transition temperature of the polymer is $-54°C$, as determined by differential thermal analysis.

EXAMPLE 3

Example 2 is repeated, except that 1,2-dimethoxyethane is susbtituted with ethylene glycol monomethyl ether. There is obtained 19 g of polybutadiene containing 65% of 1,2-units and 35% of cis-1,4 units. The intrinsic viscosity of the polymer is 0.97 dl/g.

EXAMPLE 4

Example 1 is repeated except that allyl trifluoracetate is substituted with an equivalent amount of methyl trifluoracetate. There is obtained a compound of the formula

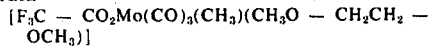
[F$_3$C — CO$_2$Mo(CO)$_3$(CH$_3$)(CH$_3$O — CH$_2$CH$_2$ — OCH$_3$)]

65 g of 1,3-butadiene in 100 ccm of toluene are added to 1.4g of this compound, and the mixture is stirred at 50°C for 24 hours. 11g of polymer are obtained. The latter has the same microstructure as the polymer of example 1; its intrinsic viscosity is 2.08 dl/g.

EXAMPLE 5

Example 1 is repeated except that 1,2-dimethoxyethane is substituted with 378 ccm of tetrahydrofuran, 5 g of yellow powder are obtained whose elemental analysis conforms to the chemical composition (MoC$_{13}$H$_{17}$O$_7$F$_3$). Its structure, as determined by infra-red spectrometry and magnetic nuclear resonance, is the following:

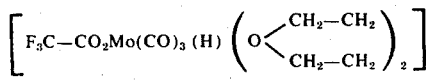

$$\left[ F_3C-CO_2Mo(CO)_3\,(H) \left( O \begin{matrix} CH_2-CH_2 \\ CH_2-CH_2 \end{matrix} \right)_2 \right]$$

The Mo — H bond of this compound is characterised by a strong infra-red absorption at 1882 cm$^{-1}$.

20 ccm of a benzenic solution of 0.6 g of tricarbonyl molybdenum hydride trifluoracetate solvated by 2 moles of tetrahydrofuran are added to a solution of 56 g of 1,3-butadiene in 300 ccm of toluene.

After stirring at 50°C for 15 minutes, there is obtained 54 g of liquid polybutadiene whose intrinsic viscosity is 0.55 dl/g. The microstructure of the polymer consists of 72% 1,2-units, 26% cis-1,4 units and 2% trans-1,4 units.

EXAMPLE 6

A solution of 0.6 g of hexacarbonyl molybdenum and 0.3 ccm of allyl trifluoracetate in 22 ccm of tetrahydrofuran is maintained under inert atmosphere at 70°C for 8 hours. It is then evaporated to dryness under reduced pressure. 14 grams of 1,3-butadiene in 73 ccm of toluene are added thereto. After 15 minutes at 50°C, there is obtained a substantially complete conversion to polybutadiene consisting of 73% of 1,2-units and 27% of cis-1,4 units. The intrinsic viscosity of the polymer is 0.77 dl/g, and its vitrous transition temperature is about −58°C.

EXAMPLE 7

A mixture of 3.9 g of hexacarbonyl molybdenum, 4,8 ccm of allyl trifluoracetate and 148 ccm of ethylene glycol monomethyl ether is heated at 60°C for 4 hours. By crystallization at −20°C as described in example 1, there is obtained 3.2 g of a yellow-orange solid consisting of a mixture of π-allyl di-carbonyl molybdenum trifluoracetate and tri-carbonyl molybdenum hydride trifluoracetate solvated with one molecule of ethylene glycol monomethyl ether.

EXAMPLE 8

10 g of hexacarbonyl molybdenum are added to a solution of 9.6 ccm of allyl trifluoracetate in 378 ccm of 1,2-dimethoxy ethane contained in a quartz reactor. The mixture is irradiated at 0°C, under weak argon stream, for 4 hours, by means of a Phillips HPR 125 lamp; it is then cooled down to about −50°C and the lighter phase is decanted and concentrated by half under reduced pressure. Normal heptane is added at 0°C up to a light opalescence of the solution; the mixture is reheated up to 20°C and then crystallized at −20°C for 24 hours. The resulting crystals are filtered off, washed several times with normal heptane and dried under reduced pressure. There are finally obtained 7 grams of the product of example 1, i.e. π-allyl di-carbonyl molybdenum trifluoracetate, solvated by one molecule of 1,2-dimethoxy ethane.

EXAMPLE 9

A solution of 14 grams of hexacarbonyl tungsten of the formula W(CO)$_6$ and 5.3 ccm of allyl trifluoracetate in one liter of 1,2-dimethoxyethane is stirred at 80°C for 4 hours in an argon stream. The solution is then cooled down to −70°C and decanted; it is concentrated under reduced pressure by evaporating ⅔ of the solvent and crystallized at −15°C for 24 hours. The resulting orange crystals are isolated by filtration and recrystallized from dioxane. The compound has the following structure, as determined by infra-red spectrometry and nuclear magnetic resonance:

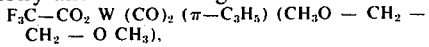
F$_3$C—CO$_2$ W (CO)$_2$ (π—C$_3$H$_5$) (CH$_3$O — CH$_2$ — CH$_2$ — O CH$_3$), which is also confirmed by the X-ray diffraction pattern of the compound.

EXAMPLE 10

A solution of 7.5 ccm of allyl trifluoracetate in one liter of 1,2-dimethoxyethane is added to 14 g of hexacarbonyl tungsten W(CO)$_6$ in a quartz reactor. The mixture is irradiated by means of a Phillips HPR 125 lamp. The reaction product is isolated as described in example 8 and there are obtained 13 g of yellow-orange crystals the elemental analysis of which conforms to the chemical composition WC$_9$H$_{11}$O$_7$F$_3$ and the structure of which, such as determined by infra-red absorption and NMR chemical displacements, is in favor of the compound:

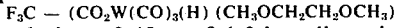
F$_3$C — (CO$_2$W(CO)$_3$(H) (CH$_3$OCH$_2$CH$_2$OCH$_3$)

A solution of 42 g of 1,3-butadiene in 65 ccm of toluene is added to 1.2 gram of this compound. After 3 hours reaction at 30°C, there are obtained 35 grams of liquid polybutadiene containing 88% of 1,2-units and 12% of cis-1,4 units. The intrinsic viscosity of the polymer, when dissolved in toluene, is 0.23 dl/g.

EXAMPLE 11

A solution of 1.4 gram of tungsten hexacarbonyl W(CO)$_6$ and 0.8 ccm of allyl trifluoracetate in 100 ccm of 1,2-dimethoxy ethane, contained in a quartz reactor, is irradiated at 0°C with a Phillips HPR 125 lamp. After evaporation of the reaction mixture under reduced pressure, the residue is taken up with a solution of 54 g of 1,3-butadiene in 80 ccm of toluene. After 3 hours stirring at 30°C, there are obtained 32 g of polybutadiene whose intrinsic viscosity is 0.2 dl/g, and microstructure thereof consists of 83% of 1,2-units and 17% of cis-1,4 units.

EXAMPLE 12

Example 11 is repeated, except that 1,3-butadiene is substituted with an equivalent amount of isoprene. There are obtained, after 8 hours at 50°C, 11 grams of polyisoprene whose microstructure consists of 67 % of 3,4-units and 33 % of 1,4-units.

EXAMPLE 13

Example 12 is repeated, except that isoprene is substituted with an equivalent amount of styrene, yielding 31 g of polystyrene whose intrinsic viscosity is 0.35 dl/g.

EXAMPLE 14

Example 12 is repeated except that isoprene is substituted with an equivalent amount of methyl methacrylate, thus yielding 8 g of methyl poly-methacrylate.

EXAMPLE 15

Example 11 is repeated except that 1,3-butadiene is substituted with an equivalent amount of 1,5-cyclooctadiene. Tungsten is used with an equivalent molar proportion of dichloromonoethylaluminum. After 3 hours at 30°C, 13 g of essentially linear polybutadiene are obtained, the intrinsic viscosity of which is 0.35 dl/g. The microstructure of the polymer consists of 80% of cis- 1,4 units and 20% of trans 1,4-units.

EXAMPLE 16

Example 15 is repeated, except that 1,5-cyclooctadiene is substituted with an equivalent amount of cyclopentene, thus yielding 28 g of mainly trans 1,5-polypentenamer.

EXAMPLE 17

A solution of 1 g of hexacarbonyl molybdenum, 0.5 cm$^3$ of allyl trifluoracetate and 2 cm$^3$ of 1,2-dimethoxy ethane in 35 cm$^3$ of cyclohexane is heated at 80± 2°C for 4 hours. 24 g of 1,3-butadiene are added thereto and the reaction mixture is stirred at 50°C for 1 hour. Methyl alcohol is added and 18 g of polybutadiene are isolated, which consist of 72% of 1,2-units, 26% of cis-1,4 units and 2% of trans1,4 units.

EXAMPLE 18

A mixture of 1 g of hexacarbonyl molybdenum, 1 cm$^3$ of allyl trifluoracetate and 4 cm$^3$ of 1,2-dimethoxyethane in 56 cm$^3$ of normal heptane is irradiated at 0°C with a HPR 125 Phillips lamp. After 4 hours, 40g of 1,3-butadiene are added and the mixture is stirred at 34°C for 30 minutes. 36.5 g of polybutadiene are obtained, the intrinsic viscosity of which is 0.39 dl/g and the microstructure of which consists of 70% of 1,2-units and 30% of cis-1,4 units.

EXAMPLE 19

45 cc of allyl trifluoracetate, $CF_3 COO C_3H_5$, is added to a solution of 75 g of molybdenum hexacarbonyl, Mo $(CO)_6$, in 705 cc of tetrahydrofuran. The solution is refluxed for 12 hours in an argon atmosphere and then, evaporated to dryness, under a reduced pressure. There is obtained 105 g of a yellow crystalline solid which is the $\pi$-allyl complex of trifluoracetate molybdenum tricarbonyl solvated by one molecule of tetrahydrofuran. The elemental analysis shows the following composition: 35.4 percent carbon, 14.1 percent fluorine, 23.6 percent oxygen and 23.7 percent molybdenum. This corresponds to the calculated composition of the compound Mo $C_{12} H_{13} O_6 F_3$. Infrared and NMR spectra exhibit bands characteristic for carbonyl trifluoracetate and $\pi$-allyl groups, as well as for a coordinated tetrahydrofuran molecule; they support the following formula: $(CF_3COO) Mo (CO)_3 ( \pi\text{-}C_3H_5)$.

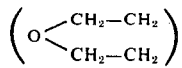

3.25 g of this material is dissolved in 40 cc of benzene; the solution is heated at 60°C for 3 hours in admixture with a solution of 720 g of butadiene in 2100 cc of toluene. The polymer formed is then precipitated from the reaction mixture by adding isopropryl alcohol; it is then filtered and dried under vaccum. 660 g of polybutadiene is obtained, containing 75% of vinyl units, 23% of cis-1,4 units and 2% of trans 1.4 units. The number average molecular weight or determined by osmometry is 50,000 with a molecular weight distribution, given by the Mw/Mn ratio, of 2.3.

EXAMPLE 20

20 g of the complex of Example 19 is dissolved in 200cc of methyl ethylketone at room temperature. The solution is evaporated to dryness. The elemental analysis of the yellow powder obtained is similar to that of the starting material and it corresponds to the composition (Mo $C_{12} H_{13} O_6 F_3$). But infrared and NMR spectra show that one molecule of methylethylketone has been substituted for the tetrahydrofuran molecule in the compound of Example 19, this yielding a new complex having the formula $CF_3 COO Mo (CO)_3 (\pi\text{-}C_3H_5).(CH_3 CO CH_2 CH_3)$, which is a catalyst for the polymerization of butadiene.

EXAMPLE 21

Figure 2:
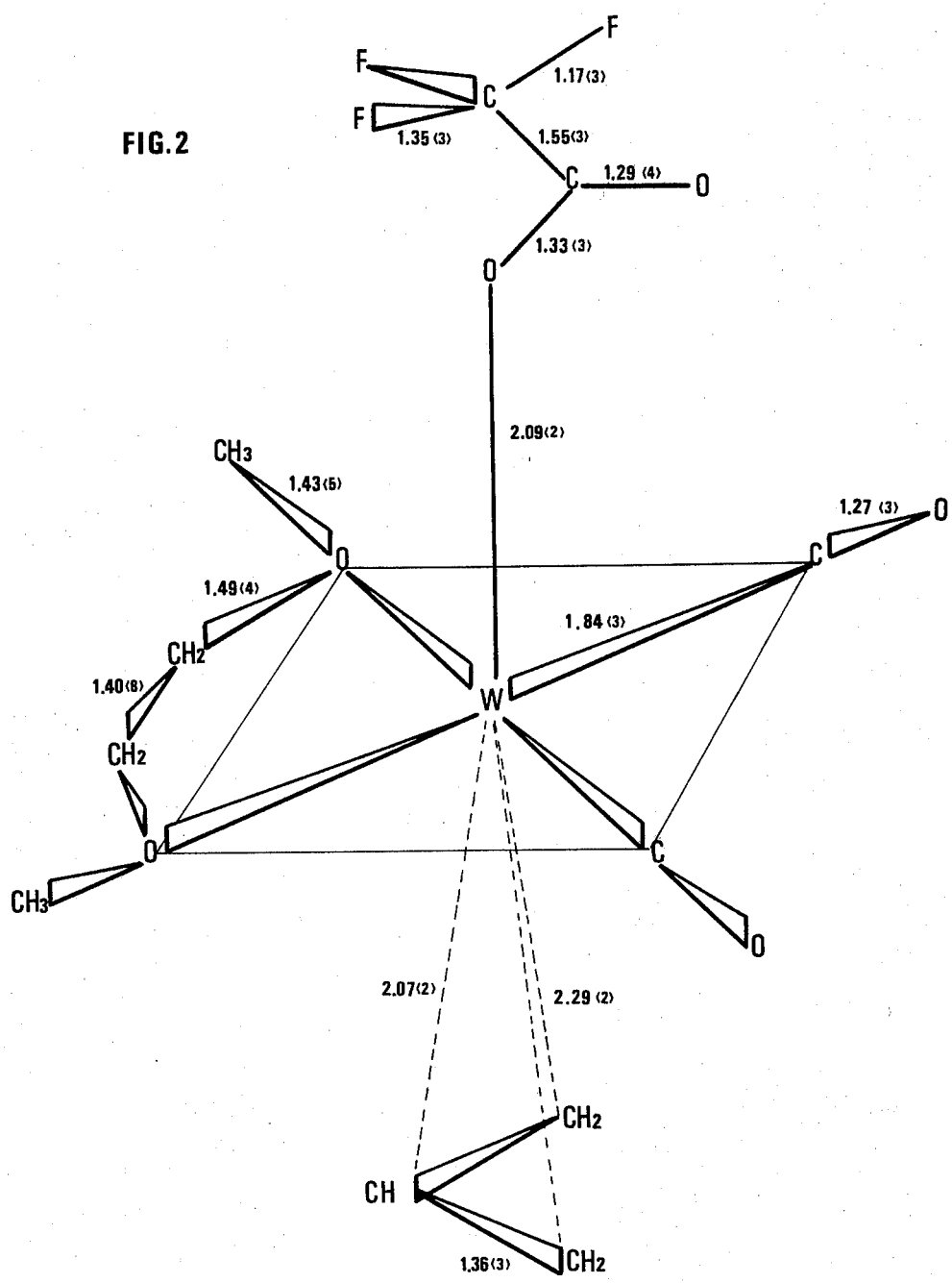

A solution comprising 4 cc of allyl trifluoracetate in a mixture of 8 g of molybdenum hexacarbonyl and 1000 cc of acetone is refluxed for 22 hours in an argon atmosphere. The solution is then evaporated to dryness under a reduced pressure. Quantitative yield of the compound of the formula $(CF_3COO) Mo (CO)_3 (\pi\text{-}C_3 H_5) (CH_3CO CH_3)$ is reached. A mixture of 0.58 g of this material with 200 cc of toluene and 130 g of butadiene is stirred at 60°C for 15minutes and then precipitated by the addition of isopropylalcohol. There is obtained 7 g of polybutadiene the microstructure of which consists of 77% 1,2 units, 18% cis 1,4 units, and 5% trans 1,4 units; the intrinsic viscosity, ad determined at 30°C in toluene, is 0.52 dl/g. The spatial structure of the compounds obtained in Examples 1 and 9, as determined from their X-ray diffraction patterns is given on the accompanying drawings (FIG. 1 and FIG. 2 respectively) where the numbers indicate the intramolecular lengths in Angstrom and the bracketed numerals indicate the average uncertainty, on the determination of said lengths (expressed as hundredths Angstrom).

What we claim as this invention is:

1. A compound of the formula $[(H_{3-n}X_n)C—CO_2M(CO)_m(R)_p(L)_q]_r$ in which each X is fluorine, chlorine or bromine with the provision that at least one X is fluorine, $n$ is an integer selected from 1, 2 and 3, M is a metal selected from the group consisting of molybdenum and tungsten, R is selected from the group consisting of a hydride ion or a methyl, ethyl, allyl, methallyl, crotyl, phenyl or benzyl radical, L is a tetrahydrofuran or dioxane Lewis base, $m$ is an integer from 1 to 3 inclusive, $p$ is 1 and $q$ is an integer selected from the values 1 and 2, and $r$ is 1, with the proviso that the values of $m$, $p$ and $q$ are such that in the valence shell of said metal M the sum of the number of electrons contributed by said metal M and the number of electrons contributed by the ligands is 18.

2. A compound as defined by claim 1, in which $n$ is 3 and all X are fluorine.

3. A compound as defined by claim 1, in which R is a hydride ion.

4. A compound as defined by claim 1, in which R is $\pi$-allyl.

5. A compound as defined by claim 1, in which the Lewis base is tetrahydrofuran.

6. A compound as defined by claim 1, said compound having the formula

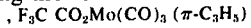

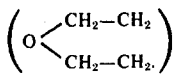

7. A compound as defined by claim 1, said compound having the formula

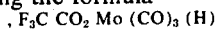

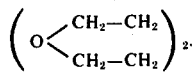

* * * * *